US00PP26113P2

(12) United States Plant Patent
Delabroye

(10) Patent No.: US PP26,113 P2
(45) Date of Patent: Nov. 17, 2015

(54) ***HEUCHERA* PLANT NAMED 'DELA 105'**

(50) Latin Name: ***Heuchera* hybrid**
Varietal Denomination: DELA 105

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 104 days.

(21) Appl. No.: 13/694,454

(22) Filed: Dec. 4, 2012

(51) Int. Cl.
*A01H 5/12* (2006.01)

(52) U.S. Cl.
USPC ..... Plt./440

(58) Field of Classification Search
USPC ..... Plt./440
CPC ..... A01H 5/02; A01H 5/12; A01H 5/00; A01H 5/025
See application file for complete search history.

(56) References Cited

PUBLICATIONS

Rice. *Heuchera* 'Magnum': new, and with huge leaves-Graham Rice' New Plants Blog posted on Aug. 22, 2011, retrieved on Jul. 29, 2014, retrieved from the Internet at <http://mygarden.rhs.org.uk/blogs/graham_rice/archive/2011/08/22/heuchera-magnum-new-and-with-huge-leaves.aspx> 2 pp.*

Upov Pluto: Plant Variety Database 20140721, retrieved on Jul. 29, 2014, retrieved from the Internet at <https://www3.wipo.int/pluto/user/en/index.jsp>, for *Heuchera magnum*, 1 page.*

Loader. Heucheraholics: New *Heucheras*, Heucherllas and Tiarellas coming to Heucheraholics soon. Heucheraholics the blog Jun. 22, 2011 retrieved from the Internet at <http://heucheraholics.blogspot.com/2011/06/new-heucheras-heucherllas-and.html> 3 pp.).*

CPVO Application for grant of Community Plant Variety Rights to the Community Plant Variety Office for *Heuchera* 'Magnum' 2012, pp. 1-7.*

Babylon 10 Dutch to English Translation, retrieved on Apr. 22, 2015, retrieved from the Internet at <http://translation.babylon.com/dutch/to-english/>, 2 pp.*

* cited by examiner

*Primary Examiner* — June Hwu
(74) *Attorney, Agent, or Firm* — Penny J. Aguirre

(57) ABSTRACT

A new cultivar of hybrid *Heuchera* named 'DELA 105', characterized by its leaves that are burgundy red-dark green with very dark green veins and a light silver overlay on the upper surface and solid burgundy-red on the lower surface, its leaves that are very large in size; up to 25 cm in diameter, its petioles that are burgundy red in color, and its tolerance to heat, humidity, and drought.

2 Drawing Sheets

Botanical classification: *Heuchera* hybrid.
cultivar designation: 'DELA 105'.

BACKGROUND OF THE INVENTION

The present invention relates to a new and distinct cultivar of *Heuchera* of hybrid origin, botanically known as a *Heuchera* and is hereinafter referred to by its cultivar name 'DELA 105'.

The new cultivar was discovered as a whole plant mutation by the Inventor in Hantay, France. The Inventor sowed seeds that were pooled from crosses made between proprietary plants in his breeding program in 2008. The Inventor selected 'DELA 105' in 2010 as a single unique plant amongst the seedlings that resulted from the above crosses. The exact parentage is unknown.

Asexual propagation of the new cultivar was first accomplished by the Inventor by division in Hantay, France in 2011. Asexual propagation of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'DELA 105' as a new and unique cultivar of *Heuchera*.

1. 'DELA 105' exhibits unique foliage with leaves that are burgundy red-dark green with very dark green veins and a light silver overlay on the upper surface and solid burgundy-red on the lower surface.
2. 'DELA 105' exhibits leaves that are very large in size; up to 25 cm in diameter.
3. 'DELA 105' exhibits petioles that are burgundy red in color.
4. 'DELA 105' is tolerant to heat, humidity and drought.
5. 'DELA 105' is hardy at least in U.S.D.A. Zones 3 to 8.

'DELA 105' is a unique *Heuchera* with foliage coloration that is unknown to exist in other cultivars of *Heuchera* known to the Inventor. 'DELA 105' can be compared most closely to 'Dark Secret' (U.S. Plant Pat. No. 20,683), 'Mocha' (U.S. Plant Pat. No. 18,386), and 'Beaujolais' (U.S. Plant Pat. No. 19,577), for their similarity in foliage coloration and in having *Heuchera*×*villosa* in its parentage. 'Dark Secret' differs from 'DELA 105' in having smaller leaves that is purple-bronze with a silver sheen rather than silvery mottling and in having petioles that are purple in color. 'Mocha' differs from 'DELA 105' in having smaller leaves that become browner in color when mature and in lacking silvery mottling. 'Beaujolais' differs from 'DELA 105' in having slightly smaller leaves that are lighter burgundy in color with lighter colored veins.

BRIEF DESCRIPTION OF THE DRAWING

The accompanying colored photographs illustrate the overall appearance and distinct characteristics of the new *Heuchera*. The photographs were taken of a plant two years in age as grown outdoors in a 10-liter container in The Netherlands.

The photograph in FIG. 1 provides a side view of the plant habit and foliage coloration of 'DELA 105'.

Figure 1:
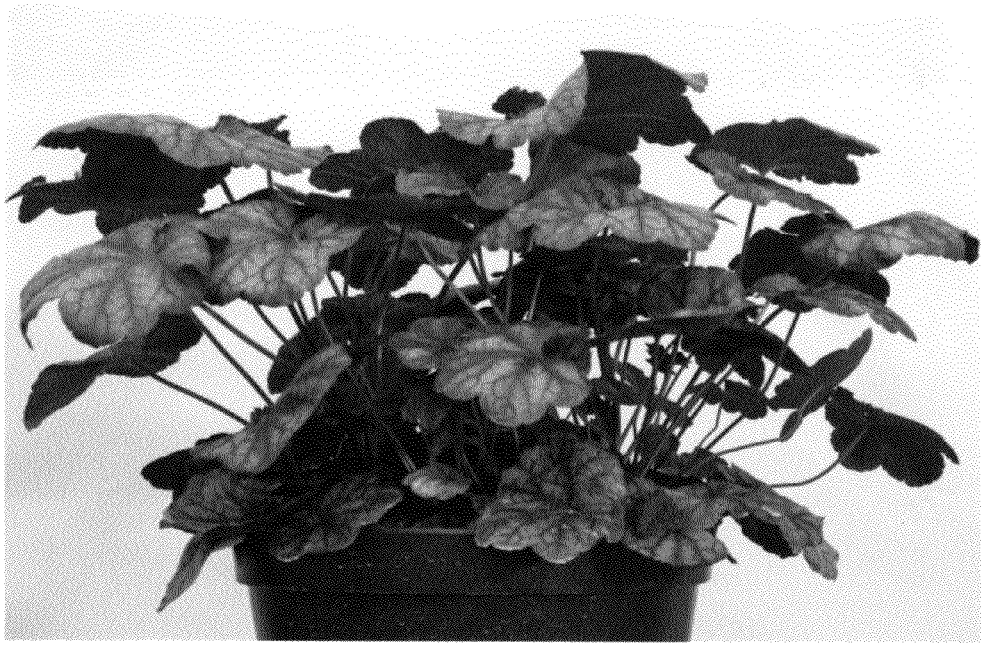
Figure 2:
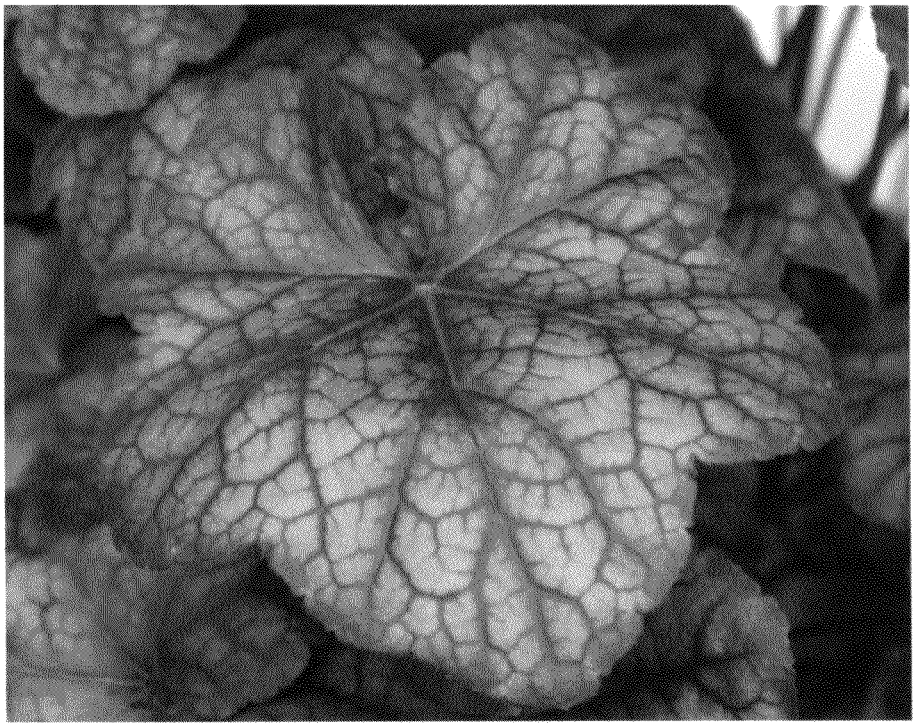

The photograph in FIG. 2 provides a close-up view of a leaf of 'DELA 105'.

Figure 3:
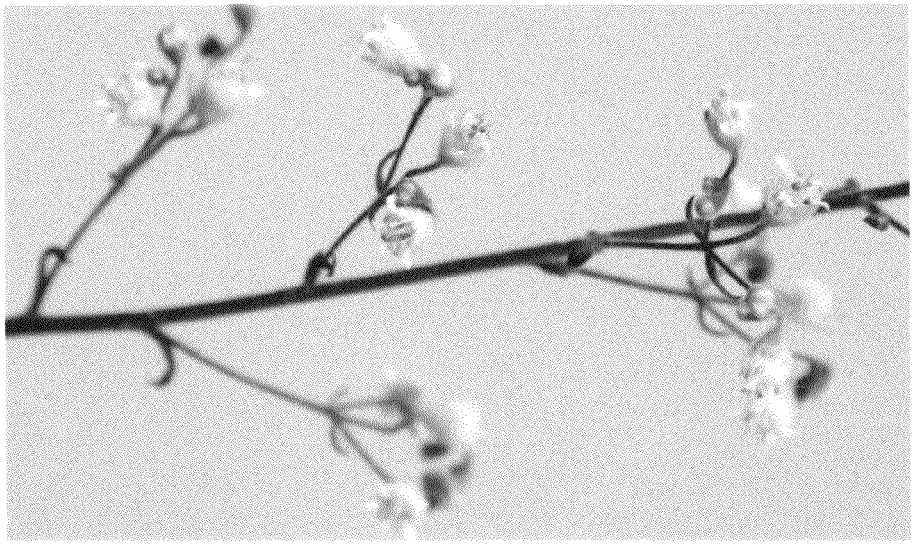

The photograph in FIG. 3 provides a view of an inflorescence of 'DELA 105'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year-old plants of the new cultivar as grown outdoors in 10-liter containers in The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Herbaceous perennial

*Plant habit*.—Clump-forming, mounded foliage.

*Height and spread*.—Flattened globular in shape, average of 28.5 cm in height from soil to top of leaves and about 58.5 cm in width.

*Hardiness*.—At least in U.S.D.A. Zones 3 to 8.

*Diseases and pests*.—Not more susceptible to pests and diseases than other *Heuchera* varieties.

*Environmental stresses*.—Has shown tolerance to heat, humidity, and drought.

*Root description*.—Fibrous roots on woody rootstalks.

*Branching habit*.—Basal rosette, no lateral branches.

*Basal branching*.—No lateral stems only basal rosettes.

*Propagation*.—In vitro propagation is the preferred method, division are also possible.

*Growth rate*.—Moderately vigorous.

Foliage description:

*Leaf shape*.—Broad ovate to orbicular.

*Leaf division*.—Simple.

*Leaf base*.—Hastate, lobes touching to slightly overlapping.

*Leaf apex*.—Rounded.

*Leaf venation*.—Laciniate, 200A in color on upper surface, N79B in color on lower surface.

*Leaf margins*.—Lobed with an average of 9 lobes per leaf, lobe margins crenate.

*Leaf attachment*.—Petiolate.

*Leaf arrangement*.—Alternate, basal rosettes.

*Leaf orientation*.—Typically nearly horizontal to slightly cupped under.

*Leaf surface*.—Upper surface slightly glossy, lower surface dull, both sides sparsely covered with short hairs, 0.5 mm in length, margins and upper surface hair color; 156D, lower surface hair color; 186D.

*Leaf color*.—Young upper surface; between 147A and N186C with mottling of 202D, young lower surface; between N77B and N186C, mature upper surface; between N187C and N200C with some mottling of 202A, mature lower surface; a blend of N79A to N79B and N186D, Primarily 177A on both surfaces.

*Leaf size*.—Average of 14 cm in length and 13 cm in width, leaves can reach up to 25 cm in diameter on mature plants.

*Leaf quantity*.—14 per basal rosette.

*Petioles*.—Round in shape, average of 22.9 cm in length and 4 mm in width, color; N186C, surface is densely covered with soft very short hairs an average of 0.3 mm in length and 156D in color.

*Stipules*.—Small leafy stipules at the base of each leaf, narrow acute apex, with an average of 1.3 cm in length and 2.5 mm in width and N186D in color.

Flower description:

*Inflorescence type*.—Compound spike.

*Inflorescence size*.—An average of 37.8 cm in height (excluding peduncle) and about 6.5 cm in width.

*Inflorescence number*.—An average of 3 compound spikes per 10-liter container.

*Flower fragrance*.—None.

*Flower quantity*.—Average of 128 per flowering stem.

*Flower lastingness*.—Average of one week.

*Flower buds*.—Broad obovate in shape, an average of 2.5 mm in diameter and 4 mm in length, 174B to 174C in color with top 159D.

*Flower aspect*.—Drooping to outward.

*Flower type*.—Single, campanulate.

*Flower size*.—About 6 mm in depth and 6 mm in diameter.

*Petals*.—About 5, rotate arrangement and implanted in the hypanthium at base, oblanceolate in shape, margin is entire, apex is acute, upper and lower surface is dull and smooth, color when opening upper and lower surface NN155A, color when fully opened upper and lower side NN155C to NN155D, about 3.5 mm in length and 1.0 mm in width.

*Calyx*.—Campanulate, sepals fused to hypanthium, 5 mm in length and 6 mm in diameter.

*Sepals*.—5, fused, campanulate hypanthium, elliptic in shape, about 5 mm in length and 1.75 mm in width, margin is entire fused into hypanthium, apex is broadly acute, fused base, surface is densely covered with very short glandular hairs about 0.1 mm in length and NN155A in color, color; immature upper surface NN155A tinged with 186D, immature lower surface 174B to 174C, mature upper surface 156D tinged with 186D, mature lower surface 156D.

*Bracts*.—None observed.

*Peduncles*.—Primary peduncle; average of 94.6 cm in length and 2.5 mm in diameter, moderate strength, held at a 0° angle (straight on top of flowering stem), color of both surfaces; 178A, secondary peduncles; average of 2.5 cm in length, 0.75 mm in diameter, moderate in strength, held at a 50° (0°=straight upright) to primary peduncle, color of both surfaces; 178A, surface sparsely pubescent.

*Pedicels*.—Average of 4 mm in length and 0.5 mm in diameter, color in between 187A and 200B, pedicel of primary flower of each spikelet straight on top of secondary pedicel, pedicels of secondary and tertiary flowers of each spikelet in an average angle of 25° (0°=straight on top of secondary peduncle), surface pubescent.

Reproductive organs:

*Gynoecium*.—2 pistils, pointed in shape, about 3.5 mm in length and 152D in color, styles are about 3 mm in length and 150D in color, ovaries are 151D in color.

*Androcoecium*.—About 5 stamens, anthers are ovate in shape, about 0.25 mm in length and 23C in color, filament 3 mm in length and NN155C to NN155D in color, pollen is low in quantity and 160D in color.

*Seed/fruit*.—No fruit or seeds detected to date.

It is claimed:

1. A new and distinct cultivar of hybrid *Heuchera* plant named 'DELA 105' as herein illustrated and described.

* * * * *